United States Patent
Martin et al.

(10) Patent No.: US 9,145,570 B2
(45) Date of Patent: Sep. 29, 2015

(54) ENZYMATIC ACYLATION METHOD USING AN ACYLPHOSPHONATE DONOR

(75) Inventors: Juliette Martin, Aramon (FR); Gerard Guillamot, Viroflay (FR); Laurent Fourage, Calvisson (FR); Denis Wahler, Caissargues (FR)

(73) Assignee: PCAS Biosolution (FR)

( * ) Notice: Subject to any disclaimer, the term of this patent is extended or adjusted under 35 U.S.C. 154(b) by 310 days.

(21) Appl. No.: 13/812,978

(22) PCT Filed: Jul. 29, 2011

(86) PCT No.: PCT/EP2011/063068
§ 371 (c)(1),
(2), (4) Date: Jan. 29, 2013

(87) PCT Pub. No.: WO2012/013765
PCT Pub. Date: Feb. 2, 2012

(65) Prior Publication Data
US 2013/0130337 A1    May 23, 2013

(30) Foreign Application Priority Data
Jul. 30, 2010   (FR) ...................................... 10 56311

(51) Int. Cl.
| C12P 7/62 | (2006.01) |
| C12P 9/00 | (2006.01) |
| C12P 11/00 | (2006.01) |
| C12P 13/02 | (2006.01) |
| C12P 17/06 | (2006.01) |

(52) U.S. Cl.
CPC .... *C12P 7/62* (2013.01); *C12P 9/00* (2013.01); *C12P 11/00* (2013.01); *C12P 13/02* (2013.01); *C12P 17/06* (2013.01)

(58) Field of Classification Search
CPC .................................. C12P 7/62; C12P 11/00
USPC .................................................. 435/135, 131
See application file for complete search history.

(56) References Cited

FOREIGN PATENT DOCUMENTS

EP        1591531        11/2005

OTHER PUBLICATIONS

International Search Report issued from PCT/EP2011/063068, dated Nov. 22, 2011.
Atmani, Abdelkrim, et al.,"Synthesis and Affiliations of Oxophosphonates in Organic Chemistry," C. R. Chimie, 2009, pp. 963-1001, vol. 12, No. 9, Elsevier Masson SAS, Paris, France.
Bjorkling, F., et al.,"Inhibition of Lipases by Phosphonates," Bioorganic & Medicinal Chemistry, 1994, pp. 697-705, vol. 2, No. 7, Elsevier Science Ltd.
Burk, Mark J., et al.,"Enantioselective Synthesis of α-Hydroxy and α-Amino Phosphonates via Catalytic Asymmetric Hydrogenation," Organic Letters, 1999, pp. 387-390, vol. 1, No. 3, American Chemical Society.
Fang, Maohai, et al.,"Succinylphosphonate Esters are Competitive Inhibitors of MenD that Show Active-Site Discrimimination between Homologous α-Ketoglutarate-Decarboxylating Enzymes," Biochemistry, 2010, pp. 2672-2679, vol. 49, No. 12, American Chemical Society.
Kafarski, Pawel, et al.,"Application of bacteria and fungi as biocatalysts for the preparation of optically active hydroxyphosphonates," Journal of Molecular Catalysis B: Enzymatic, 2004, pp. 99-104, vol. 29, No. 1-6, Elsevier B.V.
Marmor, Robert S., et al.,"The Copper-Catalyzed Decomposition of Some Dimethylphosphono-SubStituted Diazoalkanes," J. Org. Chem., 1971, pp. 128-136, vol. 36, No. 1.
McKenna, Charles E., et al.,"Recent Progress in Carbonylphosphonate Chemistry," Topics in Current Chemistry, 2002, pp. 201-238, vol. 220, Springer-Verlag.
Sekine, Mitsuo, et al.,"Acylphosphonates: P—C Bond Cleavage of Dialkyl Acylphosphonates by Means of Amines. Substituent and Solvent Effects for Acylation of Amines," J. Org. Chem., 1980, pp. 4162-4167, vol. 45, No. 21, American Chemical Society.
Sekine, Mitsuo, et al.,"Dialkyl Acylphosponates: A new Acylating Agent of Alchohols," Tetrahedron Letters, 1981, pp. 3617-3620, vol. 22, No. 37, Pergamon Press Ltd., Great Britain.

(Continued)

*Primary Examiner* — Tekchand Saidha
*Assistant Examiner* — Md. Younus Meah
(74) *Attorney, Agent, or Firm* — Banner & Witcoff, Ltd.

(57) ABSTRACT

The invention relates to an enzymatic acylation method including at least the following steps of: contacting at least one compound having at least one function selected from among the amine, alcohol, or thiol functions, at least one microorganism having an acyl transfer activity and/or an acyl transfer enzyme, and at least one acylphosphonate donor of formula (I), where: R is an alkyl, alkene, alkyne, aryl, or aralkyl radical, or is —ORa, —SRa, —NRaRb, where Ra and Rb are identical or different and are H, an alkyl, alkene, alkyne, aryl or aralkyl radical, the alkyl, alkene, alkyne, aryl or aralkyl radicals being optionally substituted; X is O or S; Y and Z, which are identical or different, are —OR1, —OR2, —SR1, —SR2, —NR'1R"1, —NR'2R"2; R1, R2, R'1, R'2, R"1 and R"2, which are identical or different, are an alkyl, alkene, alkyne, aryl or aralkyl radical, said alkyl, alkene, alkyne, aryl or aralkyl radicals being optionally substituted; and recovering the compound including at least one acyl function, said function being selected from among the amine, alcohol, or thiol functions.

Formule (I)

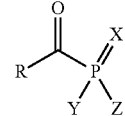

13 Claims, No Drawings

(56) References Cited

OTHER PUBLICATIONS

Xie, Xinkai, et al.,"Efficient Synthesis of Simvastatin by Use of Whole-Cell Biocatalysis," Applied and Environmental Microbiology, 2007, pp. 2054-2060, vol. 73, No. 7, American Society for Microbiology.

Burk, Mark J., et al, Organic Letters, 1, 3, 1999, 387-390.

Marmors, R. S., Journal of Organic Chemistry, 31, 1, 1971, pp. 128-136.

GenBank Accession No. AAD34555, 1999.

ENZYMATIC ACYLATION METHOD USING AN ACYLPHOSPHONATE DONOR

RELATED APPLICATION DATA

This application is a National Stage Application under 35 U.S.C. 371 of co-pending PCT application PCT/EP2011/063068 designating the United States and filed Jul. 29, 2011; which claims the benefit of FR patent application number 1056311 and filed Jul. 30, 2010 each of which are hereby incorporated by reference in their entireties.

The present invention relates to an enzymatic acylation method for the production of various organic compounds and in particular active substances, pharmaceutical intermediates, intermediates and compounds for the flavorings and fragrances industry and convenience products.

Acylation, or acyl transfer, is a reaction during which an acyl group is added to a molecule, in particular to an alcohol, amine or thiol functional group. The acyl group is in general transferred from an acylating agent.

The acylation of heteroatoms, such as O, N and/or S, can be used on organic compounds, in particular in order to activate certain functional groups in view of their transformation or of the protection of one or more functional groups.

The transformation can, for example, be the acylation of an alcohol functional group followed by the reduction of a carboxylic ester in order to give the alkane or the corresponding ether.

The protection of a functional group, in particular in relation to certain reaction conditions, can consist in the protection of an alcohol functional group in the form of an ester (the type of protection used extensively with sugars), or the protection of an amine in the form of an amide.

From a pharmaceutical perspective, the acylation of certain active ingredients can enable the synthesis of prodrugs. These prodrugs can exhibit improved bioavailability, and/or enable a wider choice of routes of administration for the drug.

For example, amide prodrugs of penicillin, ester prodrugs of cephalosporin and ester prodrugs of ibuprofen are today important therapeutic molecules.

Certain acylations can also lead to active ingredients, such the acetylation of salicylic acid giving aspirin, for which the acylated group becomes an acylating agent producing, in part, the pharmacological effect. In the case of aspirin, the analgesic, antipyretic and anti-inflammatory properties come from the irreversible inhibition by acetylation of the cyclooxygenase enzymes involved in the production of prostaglandins and thromboxanes.

The known acylation methods use either chemical catalysts or enzymatic catalysts.

The most commonly used chemical acylation agents include the acyl halides. These form potent electrophiles in the presence of Lewis acid catalysts and/or strong bases. In these chemical acylation methods, acylation takes place preferentially on the primary alcohol in relation to a secondary alcohol.

Thus, when the acylation must be carried out on a secondary alcohol, stronger bases must in general be employed, with at times unsatisfactory conversion yields.

Furthermore, when selectivity between several alcohols is sought, the use of protective groups is often required, which leads to longer synthetic pathways, for example due to additional protection-deprotection steps, and thus greater cost.

Acyl donors less reactive than acyl halides have been described, for example acyl anhydrides and carboxylic acids, however these methods generally necessitate the use of expensive, noxious and/or polluting metal catalysts, without necessarily providing the acylation with selectivity.

With a view to providing the selectivity desired to the acylation reaction, enzymatic methods have been developed, in particular for the formation of esters or amides. The enzymes described include hydrolases, which are known primarily for their hydrolysis reaction. Thus, acylation is in competition with the hydrolysis reaction, which has led to the use of anhydrous media. However, quite often the biocatalyst is deactivated by the absence of water. The control of the activity of the water has thus become a critical factor in terms of the implementation of these methods.

In addition, the acylation reaction is also in equilibrium with the reverse reaction, in which the leaving group of the acyl donor can react with the chemical functional group formed. The nucleophilicity of this leaving group is therefore very important in terms of the reversibility of the enzymatic acylation reaction. For example, if an ester or a thioester is used as the acyl donor, the reaction remains highly reversible, even if the alcohol formed is less reactive than an amine, or if the thiol released is volatile.

Thioesters have been described as acyl donors in a lipase-based method. The use of an S-ethyl-thioester, for example, makes it possible to remove the leaving group by evaporation. This can thus shift the equilibrium of the reaction toward the formation of the ester. On the other hand, these types of donors do not seem to be attractive to industry, undoubtedly due to the fact that the leaving group is noxious and malodorous.

Other acyl donors reputed to be irreversible have been developed. This is the case in particular of anhydrides and enol esters, for which the molecule released after the transfer of the acyl and the acid functional group in the first case, and the carbonyl functional group in the second case, is not nucleophilic.

However, anhydrides also can acylate the enzyme and deactivate it, and secondary reactions can take place, notably due to the difficulty controlling the acid concentration in the reaction medium.

With regard to enol-ester donors, since the irreversibility of the acylation is "guaranteed" by the keto-enol equilibrium of the leaving group, applications calling upon these reagents have been widely developed. However, as these molecules are easily hydrolysable and thus relatively unstable under the reaction conditions, the addition of a stabilizer is thus generally required for their preservation. Furthermore, the quantities of donor required, the number of impurities and the conversion yields can be factors limiting their use. Lastly, the enols released by the acyl transfer are converted into carbonyl molecules, often into volatile aldehydes, which can react with the enzyme by forming imine bonds with the surface of the protein, thus deactivating it.

The irreversibility of the acylation reaction can, optionally, be provided by the use of acyltransferase enzymes, whose specificities in terms of substrate and donor, associated with the reactivity of the active site of the enzyme, in general permit the reaction in only one direction. However, the natural acyl donors for these enzymes are complex molecules, in which the acyl functional group is activated by a coenzyme A. These donors are thus difficult to manufacture and expensive. Thus, their stoichiometric use in acyl transfer makes the corresponding methods economically not viable.

In order to solve this problem, methods for regenerating the acyl-CoA donor have been developed, for example using acyl-thioesters (EP 1 591 531). However, these methods remain very complex and require heavy economic investment, making them in general completely unsuited for industrial production, in particular on a large scale.

The use of acyl-thioester donors has been proposed as alternatives to the use of acyl-CoA donors with acyltransferases. Indeed, certain observations have suggested the formation of an acyl-enzyme intermediate via a cysteine residue of the active site, and implied the possibility of using simple thioesters as acyl donors. Since this discovery, numerous acyl-thioesters have been described for the enzymatic acylation of organic compounds with an acyltransferase, but they have required somewhat complicated development and optimization research. For example, in one of these systems, the host cell had to be engineered to avoid the degradation of the thioester donor.

Furthermore, the release of highly reactive thiol compounds remains a problem. Indeed, these compounds are generally noxious and malodorous, and their nucleophilicity can lead to cleavage reactions involving the ester formed, i.e., chemical reversibility, or to degradation on another part of the molecule.

Thus, in general, chemical acylation methods have major disadvantages, in particular insofar as they can be long, expensive, noxious, polluting, characterized by an unsatisfactory yield and/or insufficiently selective.

Enzymatic acylation methods have disadvantages, too, in particular insofar as they can be complex and delicate to implement, can require expensive, noxious, polluting, foul-smelling acylating agents in order to be reversible, can cause the formation of a nucleophilic leaving group, can provide an unsatisfactory yield, and/or can use unstable reagents or acylating agents or reaction products reacting with the enzyme.

The invention thus aims to solve, in whole or in part, the problems mentioned above, and in particular aims to provide an acylation method that is efficient, ecologically sound, economically advantageous, simple, suitable for industrial production, inexpensive, specific and/or not requiring the use of noxious, malodorous and/or nucleophilic compounds.

Thus, according to a first aspect, the invention has as an object an enzymatic acylation method including at least, indeed comprising, the following steps consisting of:

a) contacting
  at least one compound including at least one functional group selected from the amine, alcohol and thiol functional groups,
  at least one microorganism having an acyl transfer activity and/or an acyl transfer enzyme, and
  at least one acylphosphonate donor of the following formula (I):

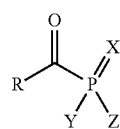

Formula (I)

in which
R is an alkyl, alkene, alkyne, aryl or aralkyl radical or is $-OR_a$, $-SR_a$, $-NR_aR_b$, in which $R_a$ and $R_b$, identical or different, are H, an alkyl, alkene, alkyne, aryl or aralkyl radical, said alkyl, alkene, alkyne, aryl and aralkyl radicals being optionally substituted,
X is O or S,
Y and Z, identical or different, are $-OR_1$, $-OR_2$, $-SR_1$, $-SR_2$, $-NR'_1R''_1$, $-NR'_2R''_2$, $R_1, R_2, R'_1, R'_2, R''_1$ and $R''_2$, identical or different, are an alkyl, alkene, alkyne, aryl or aralkyl radical, said alkyl, alkene, alkyne, aryl and aralkyl radicals being optionally substituted, and b) recovering the compound including at least one acylated functional group, said functional group being selected from the amine, alcohol or thiol functional groups.

The method according to the invention can particularly enable an acylation with an excellent stereospecificity, regiospecificity and/or chemospecificity.

In the present description, the expression "acyl transfer" is equivalent to the expression "acyl-transferase".

In the context of the present invention, "alkyl" refers to an aliphatic hydrocarbon group, which can be linear, branched or cyclic.

The alkyl radical can include from 1 to 8, indeed from 1 to 6 carbon atoms. Among the alkyl radicals mention may be made of methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc.

In the context of the present invention, "alkene" refers to an unsaturated hydrocarbon group that includes at least one carbon-carbon double bond, which can be linear, branched or cyclic.

The alkene radical can include from 2 to 8, indeed from 2 to 6 carbon atoms. Among the alkene radicals mention may be made of propene, butene, pentene, etc.

In the context of the present invention, "alkyne" refers to an unsaturated hydrocarbon group that includes at least one carbon-carbon triple bond, which can be linear, branched or cyclic.

The alkyne radical can include from 2 to 8, indeed from 2 to 6 carbon atoms. Among the alkyne radicals mention may be made of propyne, butyne, pentyne, etc.

In the context of the present invention, "aryl" refers to a compound including at least one aromatic ring, optionally heteroaromatic. Said aryl can be substituted, in particular by at least one halogen atom. Among the aryls mention may be made of phenyl, biphenyl and pyridinyl.

Aryls can include from 4 to 25 carbon atoms and optionally one or more heteroatoms, such as O, N or S.

More particularly, the aryls include one or two aromatic rings.

In the context of the present invention, "aralkyl" refers to an aryl compound including at least one substitution by an alkyl, alkene or alkyne radical. Among the aralkyls mention may be made of benzyl, methoxybenzyl, etc.

The alkyl, alkene, alkyne, aryl or aralkyl radicals can be substituted, in particular by:
  at least one halogen atom, such as F, Cl, Br and I,
  at least one amine functional group, in particular secondary or tertiary, particularly including one or more protective groups,
  at least one carbonyl functional group, such as aldehyde or ketone, in particular in protected form, for example in acetal form, and/or
  at least one ether and/or thioether functional group.

The protective groups can in particular be those described in the work by T. W. Green, P. G. M. Wuts, *Protective Groups in Organic Synthesis*, Wiley-Interscience, New York, 1999.

Furthermore, the alkyl, alkene or alkyne radicals can be interrupted by a heteroatom, notably O, N, S or P, and thus correspond, for example, to ethers, amines or thioethers.

Surprisingly, the present method uses acylphosphonates, which prove to be very good acyl donors, although they are described as being enzyme inhibitors. Furthermore, the synthesis of acylphosphonate donors is economical and simple. An example of the synthesis of these compounds is provided by Burk Mark J., Stammers Timothy A., Straub Judith A., Organic Letters, 1, 3, 1999, p. 387-390; Marmors R. S., Journal of Organic Chemistry, 31, 1, 1971, p. 128-136).

The method of the invention is in particular highly useful for the acylation of various organic compounds and in particular active substances, pharmaceutical intermediates, intermediates and compounds for the flavorings and fragrances industry and convenience products.

The enzyme used in the method can be an acyltransferase and/or a hydrolase.

The acyltransferase enzymes can belong to enzyme class (EC) 2.3.1.x according to the enzyme classification recommended by the Nomenclature Committee of the International Union of Biochemistry and Molecular Biology (http://www.chem.qmul.ac.uk/iubmb/), and in particular those with which the acyl group is transferred on a heteroatom, particularly selected from O, N and S.

According to a particular embodiment of the method, the acyltransferase enzyme is selected from O-acyl-transferase, S-acyl-transferase and N-acyl-transferase, and more particularly is O-acyl-transferase.

According to another embodiment, the enzyme is a hydrolase, in particular selected from esterase, lipase and amidase.

The person skilled in the art will be able to procure microorganisms expressing an acyltransferase or hydrolase activity for the implementation of the method of the invention. For example, the ExPASy (http://www.expasy.org/enzyme/enzyme-byclass.html) and BRENDA (http://www.brenda-enzymes.org/) protein databases make it possible to identify some of these microorganisms.

According to a particular embodiment, the microorganism producing an acyltransferase activity comes from *Aspergillus terreus* ATCC 20542.

The microorganism can be a transformed microorganism, in particular a microorganism not expressing an acyl transfer activity at the start. This microorganism can be transformed by the insertion of at least one sequence coding for such activity. For example, the microorganism may be *E. coli*, in particular into which are inserted three acyltransferase exons annotated LovD (GenBank accession number AAD34555), each of which being, for example, amplified individually from the genomic DNA of strain ATCC 20542.

Particularly, the acyl transfer activity, in particular from an enzyme or a microorganism, may be selected according to the targeted specificity.

The acylphosphonate acyl donor may correspond to the formula (I) in which:
X is O and Y and Z are —OR$_1$ and —OR$_2$ or —SR$_1$ and —SR$_2$ or —NR'$_1$R"$_1$ and —NR'$_2$R"$_2$, or
X is S and Y and Z are —OR$_1$ and —OR$_2$ or —SR$_1$ and —SR$_2$.

The acylphosphonate donors can more particularly be phosphonate esters of formula (II):

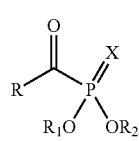

Formula (II)

in which
R, R$_1$ and R$_2$, identical or different, are an alkyl, alkene, alkyne, aryl or aralkyl radical, said alkyl, alkene, alkyne, aryl and aralkyl radicals being optionally substituted.

According to another particular embodiment, the acylphosphonate donor is a pivaloylphosphonate derivative of formula (III):

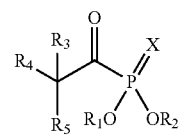

Formula (III)

in which
R$_3$, R$_4$ and R$_5$, identical or different, are an alkyl, alkene, alkyne, aryl or aralkyl radical, said alkyl, alkene, alkyne, aryl and aralkyl radicals being optionally substituted, and
R$_1$ and R$_2$, identical or different, are an alkyl, alkene, alkyne, aryl or aralkyl radical, said alkyl, alkene, alkyne, aryl and aralkyl radicals being optionally substituted, in particular R$_1$ and R$_2$ are identical, more particularly the alkyl is selected from methyl, ethyl and tert-butyl, the aryl is selected from phenyl and halophenyl, and the aralkyl is selected from benzyl, methoxybenzyl and tolyl.

Particularly, the acyl donor is ethyl 2,2-dimethylbutyrylphosphonate.

The compounds or substrates, which are in particular organic, are the acceptors of the acyl group from the acylation reaction catalyzed by an acyltransferase enzyme or a microorganism having an acyltransferase activity.

Said compound may have any structure type insofar as it is recognized as a substrate of said acyltransferase enzyme or said microorganism having an acyltransferase activity.

The compound subjected to the method thus includes at least one amine, alcohol or thiol functional group, which can be aliphatic, alicyclic or aromatic.

Thus, at least one amine, alcohol or thiol functional group, which is in particular aliphatic or alicyclic, of this compound is acylated during the implementation of the method.

In general, the structure of the compounds that accept the acyl groups is first defined in relation to the knowledge of the specificity of the acyltransferase enzyme used. However, when this substrate specificity is modified by the reaction conditions of the method, or when a mutant of this enzyme, having a substrate specificity modified by engineering, is used, an organic compound that would not be expected to be a substrate for the enzyme can be used in the method as an acyl group acceptor.

The method can enable the production of the compound [(1S,3R,7S,8S,8aR)-8-[2-[(2R,4R)-4-hydroxy-6-oxooxan-2-yl]ethyl]-3,7-dimethyl-1,2,3,7,8,8a-hexahydronaphthalen-1-yl]2,2-dimethylbutanoate from 6-(2-(1,2,6,7,8,8a-hexahydro-8-hydroxy-2,6-dimethyl-1-naphthalenyl)ethyl) tetrahydro-4-hydroxy-2H-pyran-2-one, in particular in the presence of 2,2-dimethylbutyryl-diethylphosphonate and a microorganism producing an acyltransferase activity or an acyltransferase enzyme.

According to a particular embodiment, the production of the compound [(1S,3R,7S,8S,8aR)-8-[2-[(2R,4R)-4-hydroxy-6-oxooxan-2-yl]ethyl]-3,7-dimethyl-1,2,3,7,8,8a-hexahydronaphthalen-1-yl]2,2-dimethylbutanoate is carried out in an aqueous/organic biphasic medium and particularly in a heptane/pH 5 citrate buffer mixture.

According to another of its aspects, the invention has as an object the use of acylphosphonates, in particular as described above, as an acylating agent, in particular of alcohol, thiol or amine functional groups, with an acyltransferase and/or a microorganism having an acyltransferase activity, in particular such as described above.

The examples are provided for illustration only. The characteristics described may of course be combined with each other.

EXAMPLES

Example 1

Cloning and Expression of an Acyltransferase

Each of the three acyltransferase exons annotated LovD (GenBank accession number AAD34555) was amplified individually from the genomic DNA of strain ATCC 20542 and then fused by PCR to lead to a continuous open reading frame.

The NdeI and EcoR1 restriction sites were introduced at the 5' and 3' ends, respectively.

The expression cassette was inserted into the pET26 vector (Novagen) to create the construction enabling expression.

The E. coli strain BL21 (DE3) transformed with this construction was grown on Luria-Bertani medium at 37° C. to an optical density ($OD_{600}$) of 0.5, and then 0.25 mM IPTG was added before continuing the expression for 20 hours at 20° C.

The cells were recovered by centrifugation and resuspended in pH 5.0 citrate buffer.

Example 2

Synthesis of 2,2-dimethylbutyryl-diethylphosphonate

Under inert atmosphere, 2,2-dimethylbutyryl chloride (20 g, 0.15 mol, 1 eq) is added in a double-walled reactor equipped with mechanical stirring. After having cooled to between 0-5° C., triethylphosphite (29.7 g, 0.18 mol, 1.2 eq) is added dropwise while maintaining the temperature between 0-5° C. The reaction medium (yellow solution) is then heated at 20-25° C. and left under stirring overnight. The crude mixture is then distilled to obtain the pure product: ethyl 2,2-dimethylbutyrylphosphonate (74° C. under 0.8 mbar) with a yield of 75%.

Example 3

Acyl Transfer in Whole Cells: cyclohexyl-2,2-dimethylbutanoate

A 0.5 ml cell pellet corresponding to a volume of 20 ml of culture, obtained according to example 1, is resuspended in 0.45 ml of 50 mM citrate buffer (pH 5.0) containing 10 mM $MgCl_2$ and 50 mM NaCl, and then mixed with 0.05 ml of dimethyl sulfoxide containing 100 mM cyclohexanol and 400 mM 2,2-dimethylbutyryl-diethylphosphonate.

The reaction medium is stirred at 20° C., and at regular intervals 50 μl samples are taken, diluted in 450 μl of acetonitrile and centrifuged before injection of the supernatant for the analysis and monitoring of the enzyme kinetics. Thus, 6.1% of the cyclohexanol substrate is converted into the cyclohexyl-2,2-dimethylbutanoate product after 24 hours of reaction.

The compounds are analyzed by GC-MS using a VF-5 ms silica column (L=30 m, ID=0.25 mm) impregnated with polydimethylsiloxane with 5% phenyl, with a thickness of 0.25 μm, with helium as the carrier gas and a Clarus 600 C MS. The temperature gradient was programmed as follows, with a constant flow rate of 1 ml/min helium: isotherm at 50° C. for 2 min, then increase to 280° C. by 10° C./min, then isotherm at 280° C. for 5 min.

Example 4

Acyl Transfer in Whole Cells: cis/trans-2-decahydronaphthyl-2,2-dimethylbutanoate A 0.5 ml cell pellet corresponding to a volume of 20 ml of culture, obtained according to example 1, is resuspended in 0.45 ml of 50 mM citrate buffer (pH 5.0) containing 10 mM $MgCl_2$ and 50 mM NaCl, and then mixed with 0.05 ml of dimethyl sulfoxide containing 10 mM cis/trans-2-decahydronaphthol and 40 mM 2,2-dimethylbutyryl-diethylphosphonate.

The reaction medium is stirred at 20° C., and at regular intervals 50 μl samples are taken, diluted in 450 μl of acetonitrile and centrifuged before injection of the supernatant for the analysis and monitoring of the enzyme kinetics. Thus, 6.5% of the cis/trans-2-decahydronaphthol substrate is converted into the product cis/trans-2-decahydronaphthyl-2,2-dimethylbutanoate after 24 hours of reaction.

The compounds are analyzed by GC-MS using a VF-5 ms silica column (L=30 m, ID=0.25 mm) impregnated with polydimethylsiloxane with 5% phenyl, with a thickness of 0.25 μm, with helium as the carrier gas and a Clarus 600 C MS. The temperature gradient was programmed as follows, with a constant flow rate of 1 ml/min helium: isotherm at 50° C. for 2 min, then increase to 280° C. by 10° C./min, then isotherm at 280° C. for 5 min.

Example 5

Acyl Transfer in Whole Cells: [(1S,3R,7S,8S,8aR)-8-[2-[(2R,4R)-4-hydroxy-6-oxooxan-2-yl]ethyl]-3,7-dimethyl-1,2,3,7,8,8a-hexahydronaphthalen-1-yl]2,2 dimethylbutanoate A 0.5 ml cell pellet corresponding to a volume of 20 ml of culture, obtained according to example 1, is resuspended in 0.25 ml of 50 mM citrate buffer (pH 5.0) containing 37 mM 6-(2-(1,2,6,7,8,8a-hexahydro-8-hydroxy-2,6-dimethyl-1-naphthalenyl)ethyl)tetrahydro-4-hydroxy-2H-pyran-2-one, 10 mM $MgCl_2$ and 50 mM NaCl, and then mixed with 0.25 ml of heptane containing 50 mM 2,2-dimethylbutyryl-diethylphosphonate.

The reaction medium is stirred at 20° C., and at regular intervals 50 μl samples are taken, diluted in 450 μl of acetonitrile and centrifuged before injection of the supernatant for the analysis and monitoring of the enzyme kinetics. Thus, 90% of the substrate 6-(2-(1,2,6,7,8,8a-hexahydro-8-hydroxy-2,6-dimethyl-1-naphthalenyl)ethyl)tetrahydro-4-hydroxy-2H-pyran-2-one is converted into the product [(1S,3R, 7S,8S,8aR)-8-[2-[(2R,4R)-4-hydroxy-6-oxooxan-2-yl] ethyl]-3,7-dimethyl-1,2,3,7,8,8a-hexahydronaphthalen-1-yl]2,2 dimethylbutanoate after 5 hours of reaction.

The compounds are analyzed by HPLC using a C8 analytical column (ZORBAX RX C8 250 mm×4.6 mm, 5 μm) and UV detection at 238 nm. The gradient of elution solvents used, with a flow rate of 1.5 ml/min, is as follows: (40% A+60% B) for 8 minutes, then from (40% A+60% B) to (10%

A+90% B) in 1 minute, then (10% A+90% B) for 3 minutes, then from (10% A+90% B) to (40% A+60% B) in 1 minute, then (40% A+60% B) for 7 minutes, with A=ultrapure H$_2$O+ 0.1% H$_3$PO$_4$, 85%; B=acetonitrile.

Example 6

Acyl Transfer in Whole Cells: cyclohexanemethyl-2,2-dimethylbutanoate

A 0.5 ml cell pellet corresponding to a volume of 20 ml of culture, obtained according to example 1, is resuspended in 0.45 ml of 50 mM citrate buffer (pH 5.0) containing 10 mM MgCl$_2$ and 50 mM NaCl, and then mixed with 0.05 ml of dimethyl sulfoxide containing 10 mM cyclohexanemethanol and 40 mM 2,2-dimethylbutyryl-diethylphosphonate.

The reaction medium is stirred at 20° C., and at regular intervals 50 µl samples are taken, diluted in 450 µl of acetonitrile and centrifuged before injection of the supernatant for the analysis and monitoring of the enzyme kinetics. Thus, 37.1% of the substrate cyclohexanemethanol is converted into the product cyclohexanemethyl-2,2-dimethylbutanoate after 3 hours of reaction.

The compounds are analyzed by GC-MS using a VF-5 ms silica column (L=30 m, ID=0.25 mm) impregnated with polydimethylsiloxane with 5% phenyl, with a thickness of 0.25 µm, with helium as the carrier gas and a Clarus 600 C MS. The temperature gradient was programmed as follows, with a constant flow rate of 1 ml/min helium: isotherm at 50° C. for 2 min, then increase to 280° C. by 10° C./min, then isotherm at 280° C. for 5 min.

The invention claimed is:

1. An enzymatic acylation method including at least the following steps consisting of:
   a) contacting
      at least one compound including at least one functional group selected from the group consisting of amine, alcohol and thiol functional groups,
      at least one microorganism having an acyl transfer activity of an enzyme of class EC 2.3.1.x and/or an acyl transfer enzyme of class EC 2.3.1.x, and
      at least one acylphosphonate donor of the following formula (I):

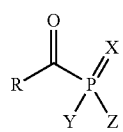

Formula (I)

in which
   R is an alkyl, alkene, alkyne, aryl or aralkyl radical being optionally substituted,
   X is O or S,
   Y and Z, identical or different, are —OR$_1$, —OR$_2$, —SR$_1$, —SR$_2$, —NR'$_1$R"$_2$, —NR'$_1$R"$_2$,
   R$_1$, R$_2$, R'$_1$, R'$_2$, R"$_1$ and R"$_2$, identical or different, are an alkyl, alkene, alkyne, aryl or aralkyl radical, said alkyl, alkene, alkyne, aryl and aralkyl radicals being optionally substituted, and b) recovering the compound including at least one acylated functional group, said functional group being selected from the group consisting of amine, alcohol and thiol functional groups.

2. The method of claim 1, wherein the acylphosphonate donor is a phosphonate ester of formula (II):

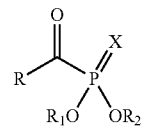

Formula (II)

in which
   R, R$_1$ and R$_2$, identical or different, are an alkyl, alkene, alkyne, aryl or aralkyl radical, said alkyl, alkene, alkyne, aryl and aralkyl radicals being optionally substituted.

3. The method of claim 1, wherein the acylphosphonate donor is a pivaloylphosphonate derivative of formula (III):

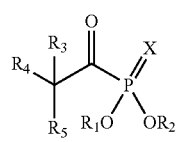

Formula (III)

in which
   R$_3$, R$_4$ and R$_5$, identical or different, are an alkyl, alkene, alkyne, aryl or aralkyl radical, said alkyl, alkene, alkyne, aryl and aralkyl radicals being optionally substituted, and
   R$_1$ and R$_2$, identical or different, are an alkyl, alkene, alkyne, aryl or aralkyl radical, said alkyl, alkene, alkyne, aryl and aralkyl radicals being optionally substituted.

4. The method of claim 1, wherein the acyl transfer activity is an acyltransferase activity.

5. The method of claim 1, wherein the acyl transfer activity is a hydrolase activity.

6. The method of claim 1, wherein the acyltransferase activity comes from *Aspergillus terreus* ATCC 20542.

7. The method of claim 1, wherein the microorganism expressing the acyltransferase activity is *E. coli*.

8. The method of claim 1, wherein the acylated compound obtained is [(1S,3R,7S,8S,8aR)-8-[2-[(2R,4R)-4-hydroxy-6-oxooxan-2-yl]ethyl]-3,7-dimethyl-1,2,3,7,8,8a-hexahydronaphthalen-1-yl]2,2-dimethylbutanoate.

9. The method of claim 1, wherein the reaction medium is an aqueous/organic biphasic medium.

10. The method of claim 1, wherein the organic solvent is heptane and/or the aqueous buffer is pH 5 citrate buffer.

11. The method of claim 1, wherein the acyl transfer activity is an acyltransferase activity selected from the group consisting of O-acyl-transferase, S-acyl-transferase and N-acyl-transferase.

12. The method of claim 1, wherein the acyl transfer activity is a hydrolase activity selected from the group consisting of esterase, lipase and amidase.

13. The method of claim 1, wherein the reaction medium is an aqueous buffer.

* * * * *